US012622802B2

(12) United States Patent
Ross

(10) Patent No.: US 12,622,802 B2
(45) Date of Patent: May 12, 2026

(54) APPARATUS AND METHOD OF USING A UROSTOMY BELT

(71) Applicant: David Patrick Ross, Hooksett, NH (US)

(72) Inventor: David Patrick Ross, Hooksett, NH (US)

( * ) Notice: Subject to any disclaimer, the term of this patent is extended or adjusted under 35 U.S.C. 154(b) by 228 days.

(21) Appl. No.: 18/540,323

(22) Filed: Dec. 14, 2023

(65) Prior Publication Data

US 2024/0341997 A1     Oct. 17, 2024

Related U.S. Application Data

(60) Provisional application No. 63/458,839, filed on Apr. 12, 2023.

(51) Int. Cl.
*A61F 5/449* (2006.01)

(52) U.S. Cl.
CPC .................................... *A61F 5/449* (2013.01)

(58) Field of Classification Search
CPC ... A61F 5/445; A61F 5/449; A61F 2005/4495
See application file for complete search history.

(56) References Cited

U.S. PATENT DOCUMENTS

| | | | |
|---|---|---|---|
| 3,822,704 A | 7/1974 | Nolan | |
| 4,596,566 A | 6/1986 | Kay | |
| 4,636,206 A * | 1/1987 | Ederati | A61F 5/44 |
| | | | 604/340 |
| 4,705,512 A | 11/1987 | Faucher | |
| 4,710,182 A | 12/1987 | Bryson | |
| 5,098,420 A | 3/1992 | Iacone | |
| 5,180,377 A | 1/1993 | Holtermann | |
| 5,618,276 A | 4/1997 | Leise, Jr. et al. | |
| 5,653,701 A | 8/1997 | Millman | |
| 5,947,942 A | 9/1999 | Galjour | |
| 6,033,390 A | 3/2000 | Von Dyck | |
| 6,840,924 B2 | 1/2005 | Buglino et al. | |
| 6,869,422 B2 | 3/2005 | Fenton | |
| 7,029,464 B2 | 4/2006 | Fenton | |
| 7,488,450 B2 | 2/2009 | Matusewicz et al. | |
| 8,096,980 B2 | 1/2012 | Cline | |
| 9,271,874 B2 | 3/2016 | Luce | |
| 9,883,965 B2 | 2/2018 | Bird et al. | |
| 10,070,987 B2 * | 9/2018 | Scott | A61F 5/449 |
| 10,463,527 B2 | 11/2019 | Gallant et al. | |
| 10,779,985 B2 | 9/2020 | Luce | |
| 11,071,640 B2 | 7/2021 | Fattman et al. | |
| 11,337,858 B2 | 5/2022 | Schwartz | |
| 11,547,594 B2 | 1/2023 | Schertiger | |
| 12,193,964 B2 * | 1/2025 | Donovan | A61F 5/443 |

(Continued)

FOREIGN PATENT DOCUMENTS

GB     2598606 A     *     3/2022     ..........     A61M 16/047

*Primary Examiner* — Rebecca E Eisenberg
*Assistant Examiner* — Gabriella E Burnette
(74) *Attorney, Agent, or Firm* — Hayes Soloway P.C.

(57) ABSTRACT

The disclosed urostomy belt includes a length of fabric having two ends. A protective unit includes a bracing member, wherein the bracing member forms a channel and is shaped to partially encircle a stoma. A shield integral with a top surface of the bracing member overlaps the channel. The protective unit is attachable to each end of the length of fabric.

12 Claims, 6 Drawing Sheets

(56) References Cited

U.S. PATENT DOCUMENTS

| | | | |
|---|---|---|---|
| 2004/0106908 A1* | 6/2004 | Leise, Jr. | ............... A61F 5/448 |
| | | | 604/355 |
| 2004/0133175 A1 | 7/2004 | Hagedorn-Olsen | |
| 2005/0256466 A1 | 11/2005 | Winkler | |
| 2006/0047256 A1 | 3/2006 | Levesque | |
| 2012/0283679 A1 | 11/2012 | Berish et al. | |
| 2013/0261577 A1 | 10/2013 | Brazeau | |
| 2017/0348140 A1 | 12/2017 | Riedel | |
| 2018/0256385 A1 | 9/2018 | Mcconnell | |
| 2020/0138619 A1 | 5/2020 | Cisko et al. | |
| 2020/0246178 A1 | 8/2020 | O'Hamill et al. | |
| 2022/0096262 A1 | 3/2022 | Austin | |
| 2022/0226143 A1 | 7/2022 | Negrete | |
| 2022/0339022 A1 | 10/2022 | Weche | |

* cited by examiner

*20*

*20*

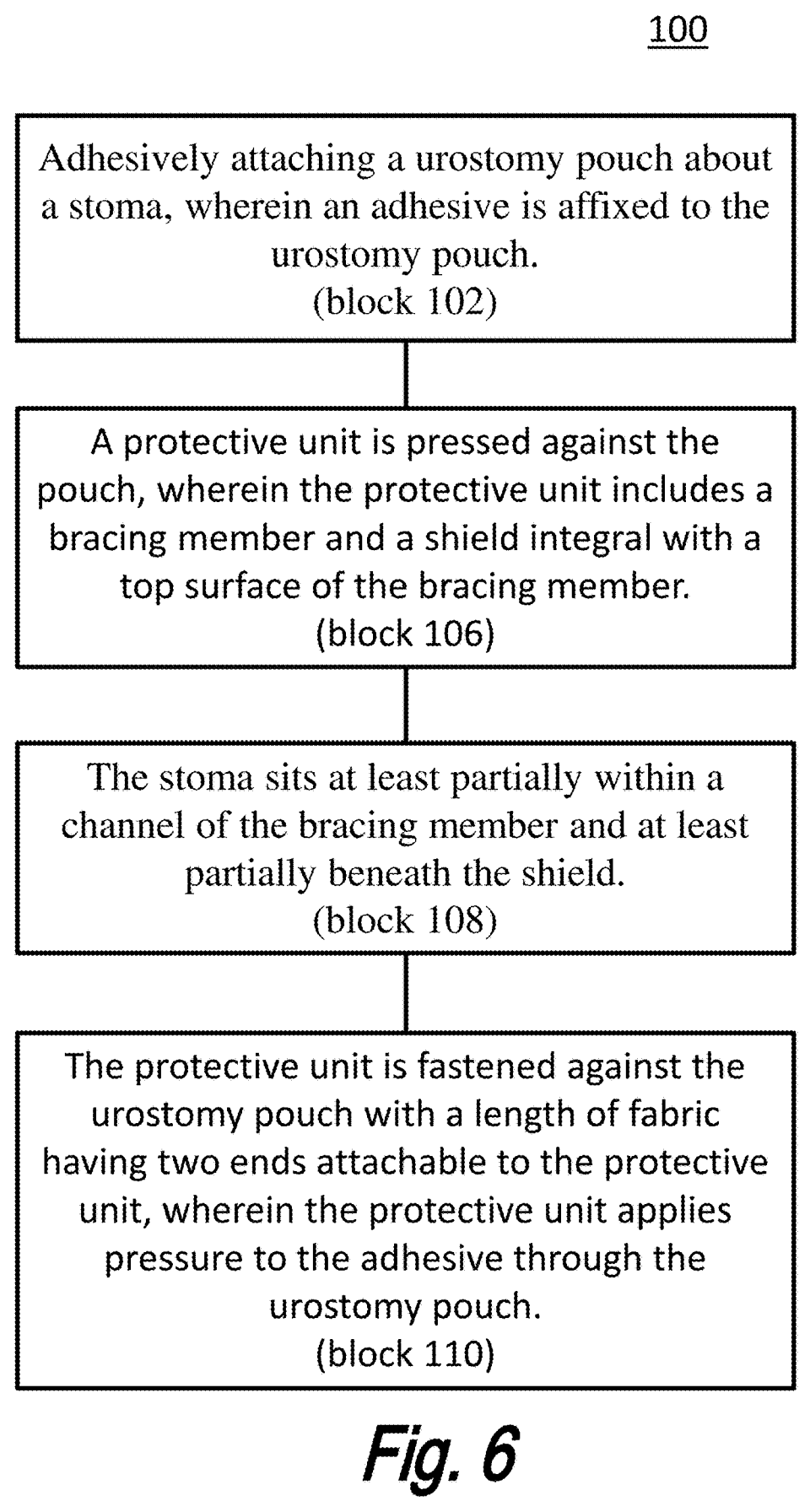

100

Adhesively attaching a urostomy pouch about a stoma, wherein an adhesive is affixed to the urostomy pouch.
(block 102)

A protective unit is pressed against the pouch, wherein the protective unit includes a bracing member and a shield integral with a top surface of the bracing member.
(block 106)

The stoma sits at least partially within a channel of the bracing member and at least partially beneath the shield.
(block 108)

The protective unit is fastened against the urostomy pouch with a length of fabric having two ends attachable to the protective unit, wherein the protective unit applies pressure to the adhesive through the urostomy pouch.
(block 110)

*Fig. 6*

APPARATUS AND METHOD OF USING A UROSTOMY BELT

CROSS-REFERENCE TO RELATED APPLICATIONS AND PRIORITY

This patent application claims priority from U.S. Provisional Patent Application No. 63/458,839 filed Apr. 12, 2023. This patent application is herein incorporated by reference in its entirety.

FIELD

This disclosure is in the field of medical devices and, more specifically, is in the field of post-surgery urostomy support devices.

BACKGROUND

A urostomy is performed when the bladder has been surgically removed or if it no longer works. Urostomy is most commonly associated with bladder cancer. During this procedure, a surgeon creates an opening in the belly just above the belt line or waist, called a stoma. A piece of the intestine is then used to remove urine from the body through that opening. For the rest of their lives, urostomy patients will only expel urine through the stoma in their belly, which will flow naturally and without any physical control.

As the urine is able to be expelled through the stoma at any time of any day, urostomy patients must wear a plastic pouch over the stoma to capture expelled urine. The pouch needs to be changed every few days or whenever it a seal is undermined or leaking. The pouch is held in place with an adhesive area that encircles the stoma. The stoma protrudes from the surface of the belly and is both sensitive and exposed. Urine will eat away at the adhesive and cause it to fail over time (often at the worst times). If the skin or pouch bunches as the bag is adhered to the skin, there may be faults in the attachment that lead to leaks. The weight of the urine in the pouch will pull at the adhesive, which is why it needs to be drained when it is one-third to one-half filled. FIG. 1 is an illustration of a urostomy pouch as is known in the prior art. Exemplary instructions for applying the ostomy pouch is here:

1. Place all materials and tools in reach while positioning the stoma area over a tub, sink, or toilet to collect any flowing fluids.
2. Cut the proper size hole in the back side of the pouch—where the adhesive area is located—to fit your particular stoma size and shape using curved scissors and avoiding cutting the bag portion of the pouch.
3. Carefully and slowly peel the adhesive area of the existing pouch from your skin using solvent-soaked wipes to minimize sticking, pulling and irritating skin and dispose of the existing pouch.
4. Clean the area all around the stoma using solvent-soaked wipes until all residue is removed, avoiding the stoma to which the solvent is an irritant.
5. Wash away the solvent with warm water only.
6. After drying, the area usually needs to be shaved carefully avoiding the stoma while shaving very close and cleaning again.
7. After fully dried, preparation fluid-soaked wipes are used to coat and protect the skin, and assist in pouch adhesion, then wait to dry.
8. Carefully place the pouch in the proper position to encircle the stoma, keeping the bag below, then holding it lightly until you can lay flat to the finish pressing in place, which needs to be done quickly and carefully, avoiding wrinkles and hold in place for a few minutes.

If the adhesive becomes detached and leaks in a public place, this process needs to be undertaken in a public restroom. Urostomy patients need a medical device that can help maintain attachment of the pouch to the skin and reduce the frequency of leaks.

SUMMARY

The present disclosure, and embodiments provided herein, discloses an apparatus and method for a urostomy belt for protecting a stoma and adhesion of a urostomy pouch. The disclosed urostomy belt includes a length of fabric having two ends. A protective unit includes a bracing member, wherein the bracing member at least partially encircles a stoma and forms a channel. A shield integral with a top surface of the bracing member overlaps the channel. The protective unit is attachable to each end of the length of fabric.

The disclosure further includes a method of applying the urostomy belt. The method includes: applying an adhesive around a stoma; pressing a urostomy pouch to the adhesive; placing a protective unit against the pouch, wherein the protective unit includes a bracing member and a shield integral with a top surface of the bracing member, and wherein the stoma sits at least partially within a channel of the bracing member and at least partially beneath the shield; and fastening the protective unit against the pouch with a length of fabric having two ends attachable to the protective unit, wherein the protective unit applies pressure to the adhesive through the pouch.

The features and advantages described herein are not all-inclusive and, in particular, many additional features and advantages will be apparent to one of ordinary skill in the art in view of the drawings, specification, and claims. Moreover, it should be noted that the language used in the specification has been selected principally for readability and instructional purposes and not to limit the scope of the inventive subject matter.

BRIEF DESCRIPTION OF THE DRAWINGS

FIG. 6 is an illustration of a flow chart for a method of applying the belt for urostomy support illustrated in FIG. 2, in accordance with the first exemplary embodiment of the disclosure.

The figures are not drawn to scale. The figures describe one embodiment of the present disclosure and are not intended to be limiting. Other embodiments within the scope of the claim requirements are contemplated. Nothing in the specification is intended to restrict the scope of the claims beyond the broadest reasonable interpretation of the claims.

DETAILED DESCRIPTION

Figure 2:
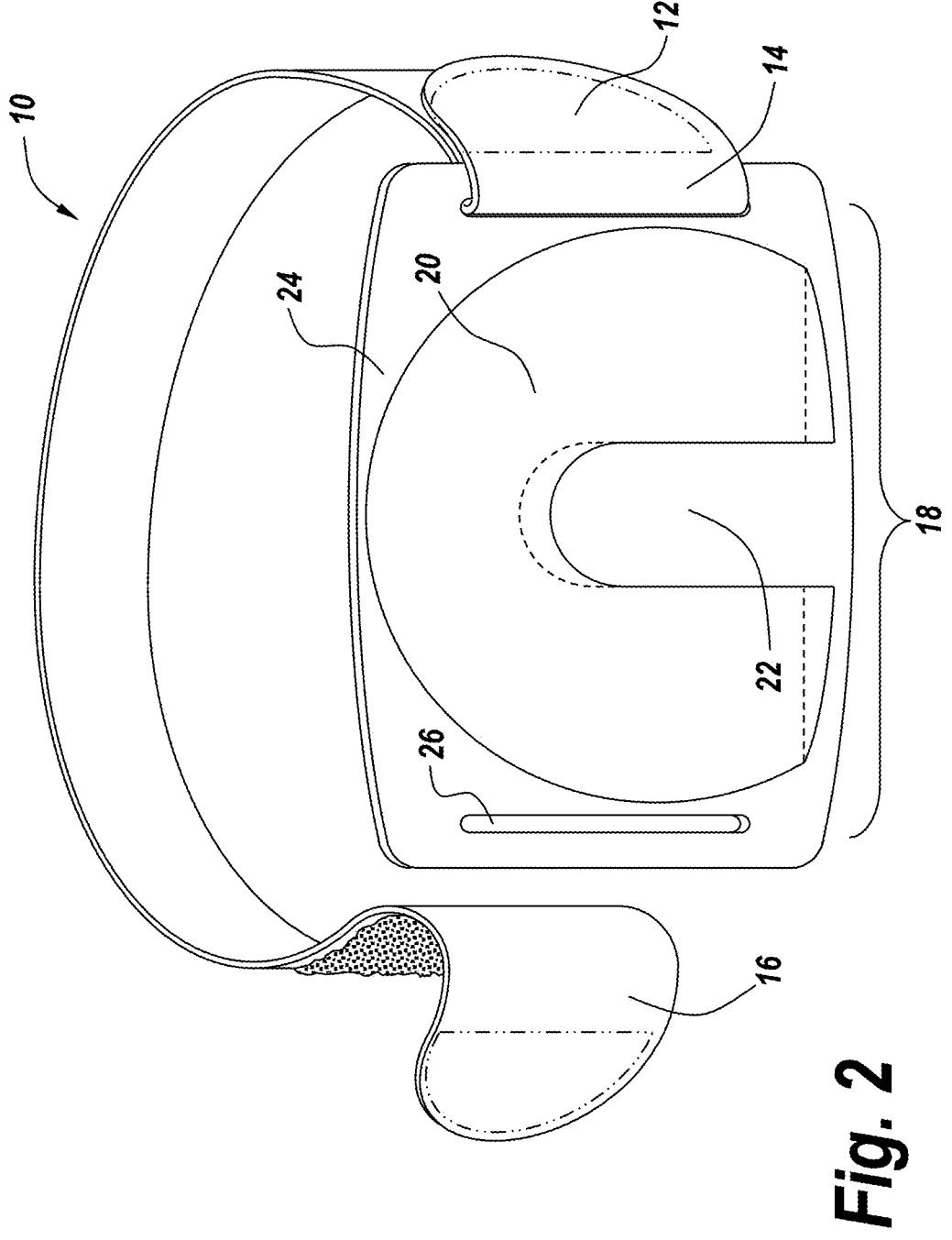
FIG. 2 is an illustration of a belt for urostomy support, in accordance with a first exemplary embodiment of the disclosure.

FIG. 2 is an illustration of a belt 10 for urostomy support, in accordance with a first exemplary embodiment of the disclosure. The disclosed urostomy belt 10 includes a length of fabric 12 having two ends 14, 16. A protective unit 18 includes a bracing member 20, wherein the bracing member 20 forms a channel 22. In the embodiment illustrated in FIG. 2, the bracing member 20 is c-shaped or horseshoe-shaped, but other shapes that partially encircle the stoma will facilitate the practice of the invention disclosed herein. Prospective shapes for the bracing member 20 may include a v-shape or something resembling 3 sides. The bracing member 20 will be in close proximity to urine for the entirety of its useful life and should not be formed of a material that absorbs urine or the smell of urine. The bracing member 20 may be made of a hydrophobic material. The bracing member may be made of a polyethylene foam. A polyethylene foam for the bracing member 20 may have a density between 1 pound and 3 pounds, may be between 1.2 and 2.2 pounds, and may preferably be approximately 1.7 pounds. A less dense material risks deformation over time while a more dense material may cause discomfort when contacting the stoma.

A shield 24 integral with a top surface of the bracing member 20 overlaps the channel 22. The shield 24 may be a rigid plastic member. The shield 24 may be translucent to allow visual inspection of the stoma or may be opaque to avoid visual inspection of the stoma. The protective unit 18 is attachable to each end 14, 16 of the length of fabric 12.

The belt 10 is for urostomy support. After a urostomy, a user will have a disposable urostomy pouch attached to the skin about a stoma with adhesive. The pouch is designed to direct urine secreted from the stoma into a bag. The belt 10 for urostomy support may help hold the bag in place, may provide support to the adhesive, and may diminish seepage of urine into the space between the pouch and skin that eats away at the adhesive or leaks onto clothing.

The length of fabric 12 is preferably a breathable material to allow a user to wear the fabric against their skin for full days with minimal irritation to the skin. The length of fabric 12 should be at least partially elastic to allow a tight fastening that does not feel restrictive. The length of fabric 12 is preferably hydrophobic to avoid absorption of urine or the scent thereof. The length of fabric 12 may be formed from a wicking material. One of the two ends 14, 16 may be looped through a slot 26 in the shield 24, folded back and attached to another section of the fabric 12 by stitching or other, similarly permanent fixing structure as known to those having skill in the art. One or both ends of the two ends 14, 16 may be looped through a slot 26 in the shield 24, folded back and removably attached to another section of the fabric, such as by a hook and loop fastener or other removable attaching structure as known to those having ordinary skill in the art. Making both ends 14, 16 of the fabric 12 removably attachable to the protective unit 18 allows the length of fabric 12 to be replaced if needed due to wear without replacing the protective unit 18. The fabric 12 may be designed in other ways known to those having ordinary skill in the art to provide the function of a belt attached to the shield 24 without departing from the scope of the present disclosure.

Figures 3A, 3B:
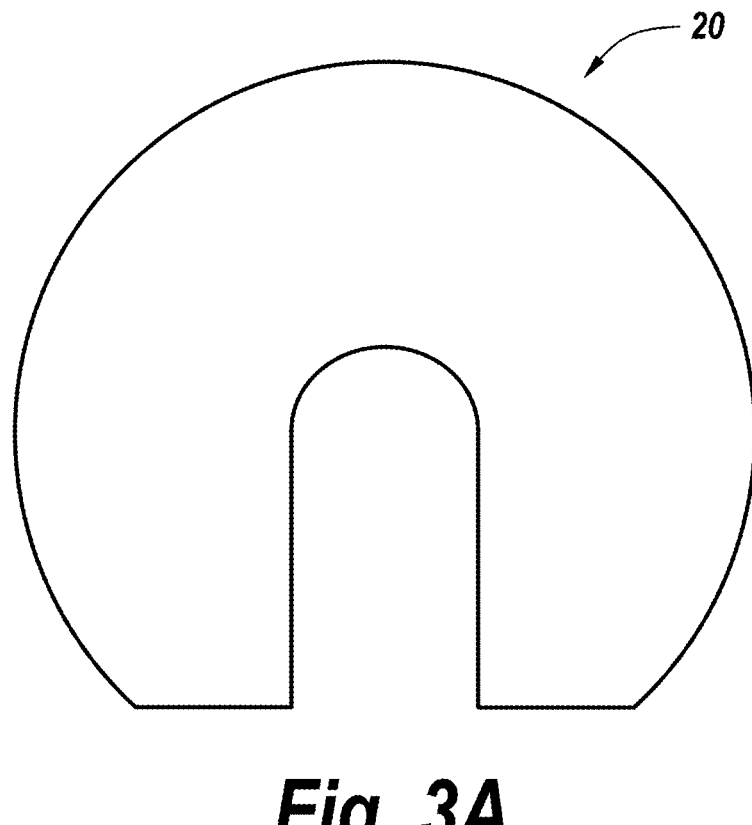
FIGS. 3A-3B are an illustration of a top plan view of a c-shaped bracket of the belt illustrated in FIG. 2, in accordance with the first exemplary embodiment of the disclosure.
Figure 4:
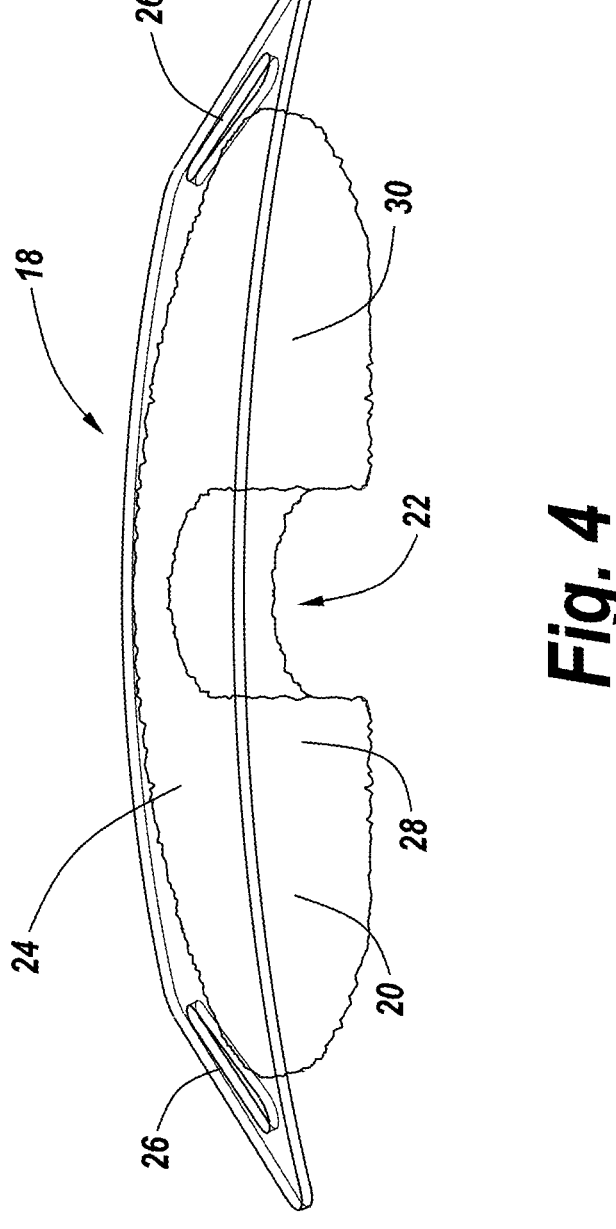
FIG. 4 is an illustration of a front perspective view of the protective unit of the belt illustrated in FIG. 2, in accordance with the first exemplary embodiment of the disclosure.

FIGS. 3A-3B are an illustration of a top plan view of a bracing member 20 of the belt 10 illustrated in FIG. 2, in accordance with the first exemplary embodiment of the disclosure. FIG. 4 is an illustration of a front perspective view of the protective unit 18 illustrated in FIG. 2, in accordance with the first exemplary embodiment of the disclosure. The bracket 20 may be formed from a soft foam or soft plastic material that allows some flexibility and is not likely to induce pain by sliding into contact with the stoma of a user, while possessing enough rigidity to maintain its shape in use. As the shield 24 is likely to bend based on its position and tension applied by the fabric 12, a top surface of the bracing member 20 may be rounded to allow the tensioned shield 24 to remain pressed against the top surface of the bracing member 20. Corners of the shield 24 may be rounded to reduce the likelihood of the shield 24 catching on things.

The bracing member 20 may include two arms 28, 30 on opposite sides of the channel 22 and the protective unit 18 may be attachable to each end 14, 16 of the length of fabric 12 proximate to each of the arms 28, 30. When worn, the channel 22 should face downward. In this position, the bracing member 20 may encircle the stoma on three sides to hold the urostomy pouch against the skin of the user and apply pressure and support to the adhesive. The channel 22 omits pressure in a space within which the urine is expected to travel from the stoma and down into the urostomy bag. Pressure applied in this location would dam or hamper proper flow of urine and increase the flow of urine into areas between the urostomy bag and the skin.

Figure 5:
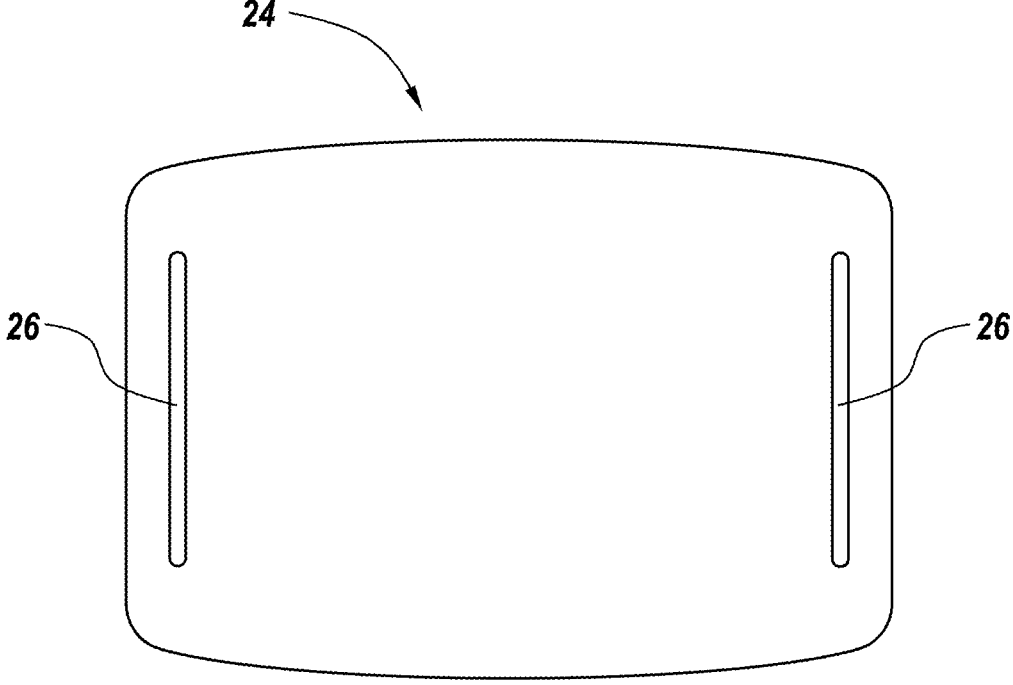
FIG. 5 is an illustration of a top plan view of a shield of the belt illustrated in FIG. 2, in accordance with the first exemplary embodiment of the disclosure.

FIG. 5 is an illustration of a top plan view of a shield 24 of the belt 10 illustrated in FIG. 2, in accordance with the first exemplary embodiment of the disclosure. The length of fabric 12 could be attached to the bracing member 20. However, applying tension from the arms 28, 30 of the bracing member 20 may cause the bracing member 20 to bend or twist in a manner that is counterproductive. The shield 24 may be a pliable, translucent plastic member shaped in a manner that resists twisting or bending from tension at the slots 26. Having a translucent shield 24 allows the user to see the stoma and observe any issues arising, such as irritation, unwanted pressure, or the like. The shield 24 may be opaque without departing from the scope of the present disclosure. An opaque shield 24 may allow some users greater discretion.

The shield 24 may be adhesively attached to the bracing member 20 or may be attached by other means known to those having ordinary skill in the art. The shield 24 and the bracing member 20 may be a single monolithic element. While illustrated as having a rectangular shape, the shield 24 may have rounded corners or rounded sides. The shape and thickness of the shield 24 may be based on the desire to minimize twisting of the edges of the shield 24 while maintaining diminished size and thickness of the shield 24.

While described herein as a product for supporting urostomy patients, the product may also be used by colostomy patients without departing from the scope of the present disclosure.

Figure 1:
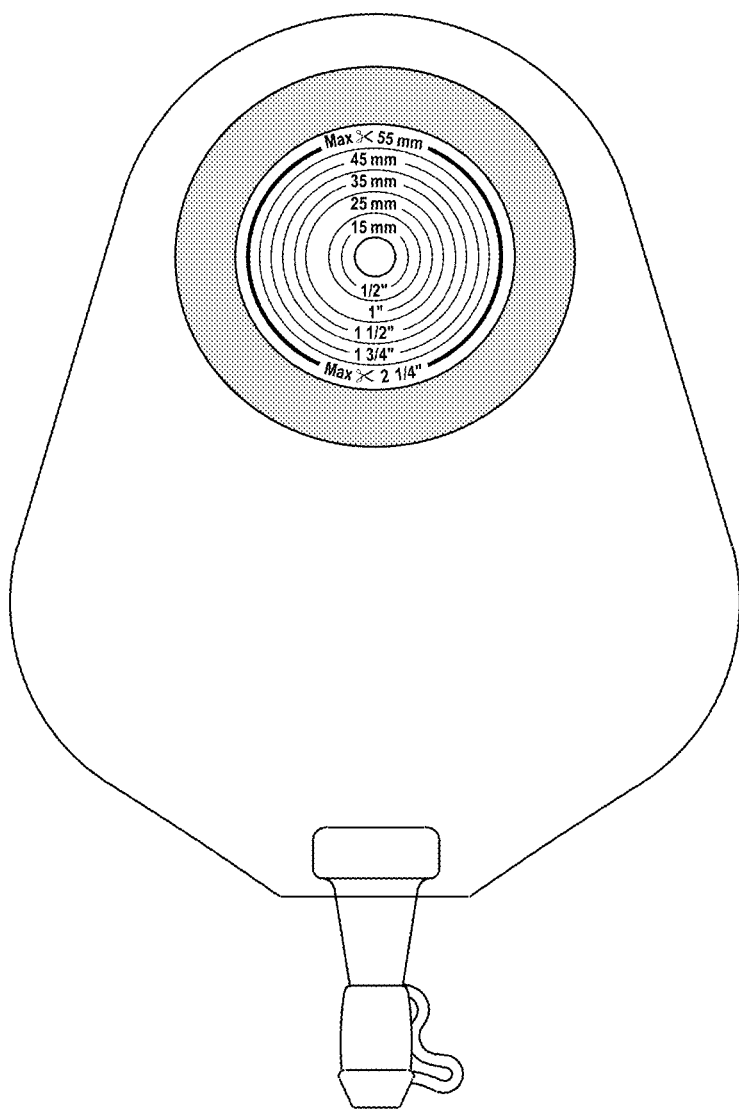
FIG. 1 is an illustration of a urostomy pouch as is known in the prior art.

FIG. 6 is an illustration of a flow chart for a method 100 of applying the belt for urostomy support illustrated in FIG. 2 over the urostomy pouch illustrated in FIG. 1, in accordance with the first exemplary embodiment of the disclosure. A pouch is adhesively positioned to collect excretion from the stoma as is known in the art (block 102). A protective unit is pressed against the pouch, wherein the protective unit includes a bracing member and a shield integral with a top surface of the bracing member (block 104). The stoma sits at least partially within a channel of the bracing member and at least partially beneath the shield (block 106). The protective unit is fastened against the pouch with a length of fabric having two ends attachable to the protective unit, wherein the protective unit applies pressure to the adhesive through the pouch (block 108).

When adhesively applying the pouch, a common requirement is to apply manual pressure to the pouch against the adhesive for a period of time while the adhesive cures. The belt may be used to have the protective unit apply even pressure to the pouch and against the adhesive while the adhesive cures. The protective unit may be manually held against the pouch to apply even pressure to the adhesive area about the stoma while the adhesive cures. As positioned, the shield 24 may protect the stoma from regular sources of irritation or discomfort, as may come from a seatbelt. Consistent application of pressure may reduce production of gaps between the pouch and the skin into which liquid may seep, adversely impacting the adhesive, irritating the skin and/or damaging clothing. There is a tendency of the area around the stoma to be herniated. This condition causes the area around the stoma to bulge outward. Wearing the protective unit applies pressure to the area around the stoma and reduces the bulge caused by the hernia.

While there have been described what are at present considered to be the preferred embodiments of this invention, it will be obvious to those skilled in the art that various changes and modifications may be made therein without departing from the invention and it is, therefore, aimed to cover all such changes and modifications as fall within the true spirit and scope of the invention.

The invention claimed is:

1. A belt for urostomy support, the belt comprising:
a length of fabric having two ends; and
a protective unit comprising:
a bracing member shaped to partially encircle a stoma, wherein the bracing member forms a channel; and
a shield integral with a top surface of the bracing member that overlaps the channel,
wherein the protective unit is attachable to each end of the length of fabric; and
wherein a thickness of the bracing member tapers from an edge proximal to the channel to an edge distal from the channel such that the bracing member is thicker proximal to the channel and thinner distal from the channel.

2. The belt of claim 1, wherein the shield is adhesively attached to the bracing member.

3. The belt of claim 1, wherein the shield is attachable to each end of the length of fabric.

4. The belt of claim 3, wherein the shield further comprises slots formed on opposing sides for receiving each end of the length of fabric.

5. The belt of claim 1, wherein the length of fabric further comprises a hook and loop fastener formed on both ends of the length of fabric for fastening the length of fabric by passage of each end of the length of fabric through the slots formed on opposing sides of the shield and wherein each hook and loop fastener extends at least partially down the length of fabric from the ends of the fabric.

6. The belt of claim 1, wherein the shield is a flat sheet of transparent, pliable plastic.

7. The belt of claim 1, wherein the shield has a flat side integral with the top surface of the bracing member and a rounded side opposite the flat side.

8. The belt of claim 1, wherein the bracing member further comprises two arms on opposite sides of the channel and the protective unit is attachable to each end of the length of fabric proximate to each of the arms.

9. A method of applying a belt for urostomy support, the method comprising the steps of:
adhesively attaching a urostomy pouch about a stoma, wherein an adhesive is affixed to the urostomy pouch;
placing a protective unit against the urostomy pouch, wherein the protective unit includes a bracing member and a shield integral with a top surface of the bracing member, and wherein the stoma sits at least partially within a channel of the bracing member and at least partially beneath the shield; and
fastening the protective unit against the urostomy pouch with a length of fabric having two ends attachable to the protective unit, wherein the protective unit applies pressure to the adhesive through the urostomy pouch;
wherein a thickness of the bracing member tapers from an edge proximal to the channel to an edge distal from the channel such that the bracing member is thicker proximal to the channel and thinner distal from the channel and is configured to provide more relative pressure to the adhesive and less relative pressure to a portion of a body of a user lacking the adhesive who is applying the belt.

10. The belt of claim 1, wherein the ends of the length of fabric are configured to pass through the slots and wrap around an edge of the shield.

11. A belt for urostomy support, the belt comprising:
a length of fabric having two ends; and
a protective unit comprising:
a bracing member shaped to partially encircle a stoma, wherein the bracing member forms a channel; and
a shield integral with a top surface of the bracing member that overlaps the channel;
wherein:
the protective unit is attachable to each end of the length of fabric;
a thickness of the bracing member tapers from an edge proximate to the channel to an edge distal from the channel such that the bracing member is thicker proximal to the channel and thinner distal from the channel;
the shield is adhesively attached to the bracing member;
the shield further comprises slots formed on opposing sides for receiving each end of the length of fabric;
the length of fabric further comprises a hook and loop fastener formed on both ends of the length of fabric for fastening the length of fabric by passage of each end of the length of fabric through the slots formed on opposing sides of the shield;
each hook and loop fastener extends at least partially down the length of fabric from the ends of the fabric; and
the bracing member is constructed from polyethylene.

12. The belt of claim 1, wherein the bracing member is constructed from polyethylene.

* * * * *